(12) United States Patent
He et al.

(10) Patent No.: US 8,977,579 B2
(45) Date of Patent: Mar. 10, 2015

(54) LATENT FACTOR DEPENDENCY STRUCTURE DETERMINATION

(71) Applicant: NEC Laboratories America, Inc., Princeton, NJ (US)

(72) Inventors: Yunlong He, Princeton, NJ (US); Yanjun Qi, Princeton, NJ (US); Koray Kavukcuoglu, Princeton, NJ (US)

(73) Assignee: NEC Laboratories America, Inc., Princeton, NJ (US)

( * ) Notice: Subject to any disclaimer, the term of this patent is extended or adjusted under 35 U.S.C. 154(b) by 251 days.

(21) Appl. No.: 13/649,823

(22) Filed: Oct. 11, 2012

(65) Prior Publication Data

US 2013/0091081 A1    Apr. 11, 2013

Related U.S. Application Data

(60) Provisional application No. 61/545,826, filed on Oct. 11, 2011.

(51) Int. Cl.
  *G06F 15/18*   (2006.01)
  *G06N 99/00*   (2010.01)
  *A61M 5/00*    (2006.01)
  *A61M 25/10*   (2013.01)
  *A61M 25/00*   (2006.01)

(52) U.S. Cl.
  CPC .............. *G06N 99/005* (2013.01); *A61M 5/007* (2013.01); *A61M 25/1011* (2013.01); *A61M 25/10* (2013.01); *A61M 25/0026* (2013.01); *A61M 2025/105* (2013.01)
  USPC .......................................................... 706/12

(58) Field of Classification Search
  CPC ......... G06N 5/003; G06N 5/046; G06F 15/18
  See application file for complete search history.

(56) References Cited

PUBLICATIONS

'Markov Random Field Modeling in Image Analysis': Li, 2009, Springer-Verlag.*
'A Generalization of Principal Component Analysis to the Exponential Family': Collins, 2001, Advances in neural. . .*
'Exponential Family Sparse Coding with Applications to Self-taught Learning': Lee, 2009, Proceedings of the Twenty-First International Joint Conference on Artificial Intelligence.*

* cited by examiner

*Primary Examiner* — Kakali Chaki
*Assistant Examiner* — Peter Coughlan
(74) *Attorney, Agent, or Firm* — Joseph Kolodka

(57) ABSTRACT

Disclosed is a general learning framework for computer implementation that induces sparsity on the undirected graphical model imposed on the vector of latent factors. A latent factor model SLFA is disclosed as a matrix factorization problem with a special regularization term that encourages collaborative reconstruction. Advantageously, the model may simultaneously learn the lower-dimensional representation for data and model the pairwise relationships between latent factors explicitly. An on-line learning algorithm is disclosed to make the model amenable to large-scale learning problems. Experimental results on two synthetic data and two real-world data sets demonstrate that pairwise relationships and latent factors learned by the model provide a more structured way of exploring high-dimensional data, and the learned representations achieve the state-of-the-art classification performance.

3 Claims, 16 Drawing Sheets

Tree

Random

| $\Phi_{i,j}(-)$ rel. | $\Phi_{i,j}(+)$ rel. | |
|---|---|---|
| | | −0.016 |
| | | −0.015 |
| | | −0.013 |
| | | −0.012 |
| | | −0.011 |
| | | −0.011 |
| 0.030 | | |
| 0.020 | | |
| 0.015 | | |
| 0.015 | | |
| 0.014 | | |
| 0.013 | | |

Precision Matrix

FIG. 3(d)

LATENT FACTOR DEPENDENCY STRUCTURE DETERMINATION

TECHNICAL FIELD

This disclosure relates generally to the field of data analysis and in particular to a method for determining descriptions of members of a large data collection that enable efficient processing of the large collections while preserving essential statistical relationships that are useful for more basic tasks such as classification, indexing or summarization.

BACKGROUND

Latent Factor Model (LFM) is a category of unsupervised methods that attempt to model observed data examples by a linear combination (coefficients) of latent unobserved variables (factors). Motivated by a desire to capture commonalities among multiple observed variables, a latent factor model has been used to explore the hidden information of the data in various areas such as psychology, bioinformatics or signal processing.

Classical latent factor models are formulated as either maximizing the variance of the factors (i.e., Principal Component Analysis (PCA)) or minimizing the error of reconstructing data by the latent factors (i.e., Matrix Factorization). The base vectors are therefore orthogonal and corresponding their coefficients are uncorrelated. Due to the simple form and computation convenience, the latent factor model has been used in modeling and analyzing data sets such as text documents and images. However, in many cases, orthogonality assumptions are so strong that it is difficult to explain the hidden factors.

Consequently, methods, structures or techniques that address such aspects would represent a significant advance in the art.

SUMMARY

An advance is made in the art according to the present disclosure directed to a general learning framework for computer implementation method we "Structured Latent Factor Analysis" (SLFA) that simultaneously learns latent factors from a data set and models the pairwise relationship between them describing the structural relationships using a sparse Gaussian graphical model. that induces sparsity on the undirected graphical model imposed on the vector of latent factors. A latent factor model SLFA is disclosed as a matrix factorization problem with a special regularization term that encourages collaborative reconstruction. Advantageously, the model may simultaneously learn the lower-dimensional representation for data and model the pairwise relationships between latent factors explicitly. An on-line learning algorithm is disclosed to make the model amenable to large-scale learning problems. Experimental results on two synthetic data and two real-world data sets demonstrate that pairwise relationships and latent factors learned by the model provide a more structured way of exploring high-dimensional data, and the learned representations achieve the state-of-the-art classification performance.

As will become apparent to those skilled in the art, a method according to the present disclosure: 1) advantageously learns higher quality similarity functions and kernels that facilitate higher performance; 2) allows for easy incorporation of past and future advances in binary classification techniques, including, but not limited to, stochastic gradient descent, sparse learning, semi-supervised learning and transfer learning; 3) has faster operation than known methods and scales to large-scale data by taking advantage in large-scale classification; 4) is simpler and easier to use than known methods; and 5) has theoretical guarantees.

BRIEF DESCRIPTION OF THE DRAWING

A more complete understanding of the present disclosure may be realized by reference to the accompanying drawings in which.

DETAILED DESCRIPTION

Figure 1:
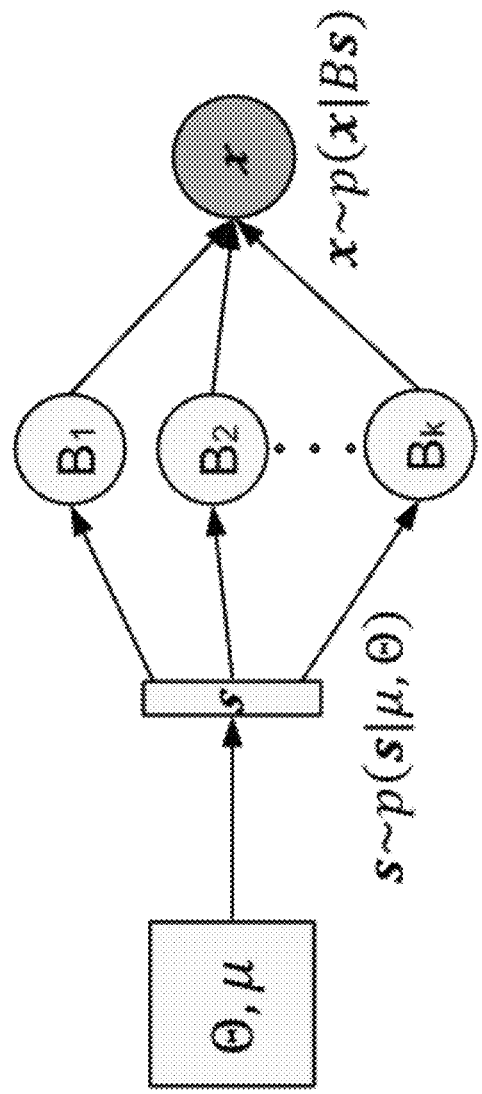
FIG. 1 is a schematic block diagram depicting an exemplary Latent Factor Network according to an aspect of the present disclosure.
Figure 2A:
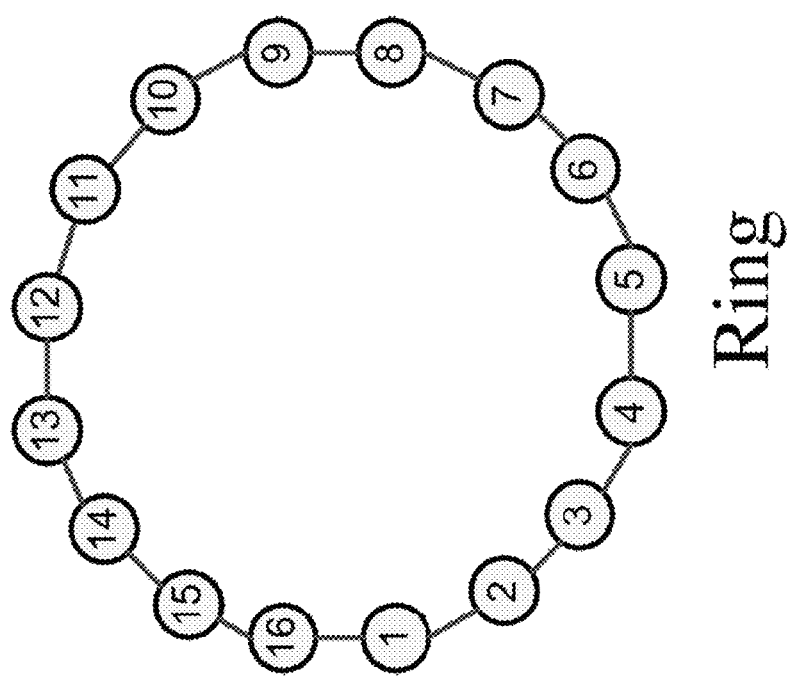
FIG. 2($a$)-2($f$) depict recovering structured latent factors from data including 2($a$) Ring; 2($b$) Grid; 2($c$) Tree; 2($d$) Random; 2($e$) F-score (ring); 2($f$) F-score (grid); 2($g$) F-score (tree); and 2($h$) F-score (random) according to an aspect of the present disclosure.
Figure 2B:
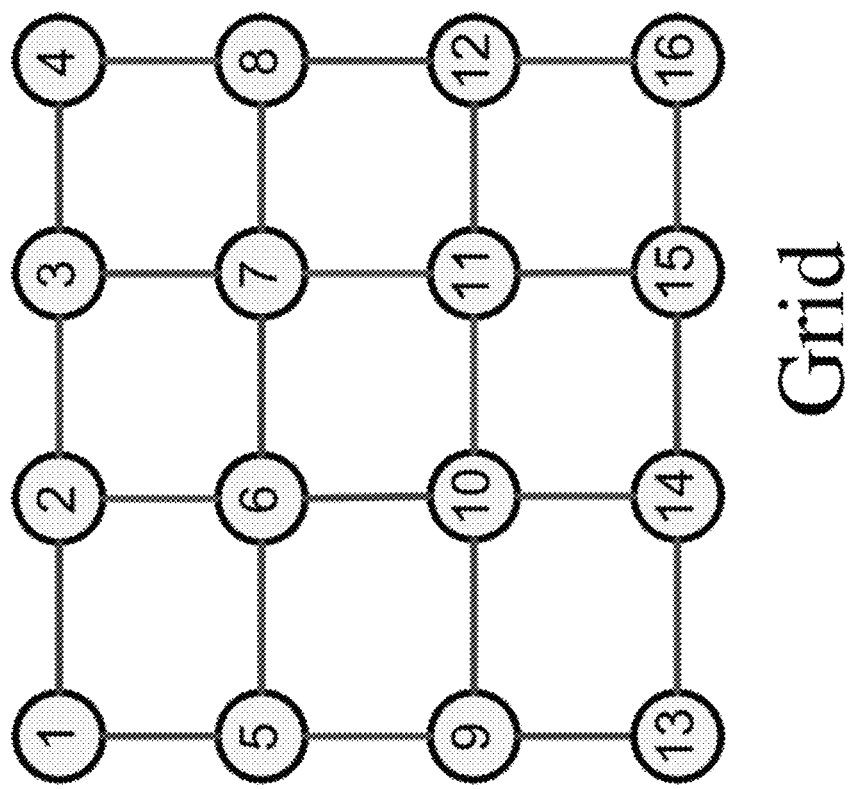
Figure 2C:
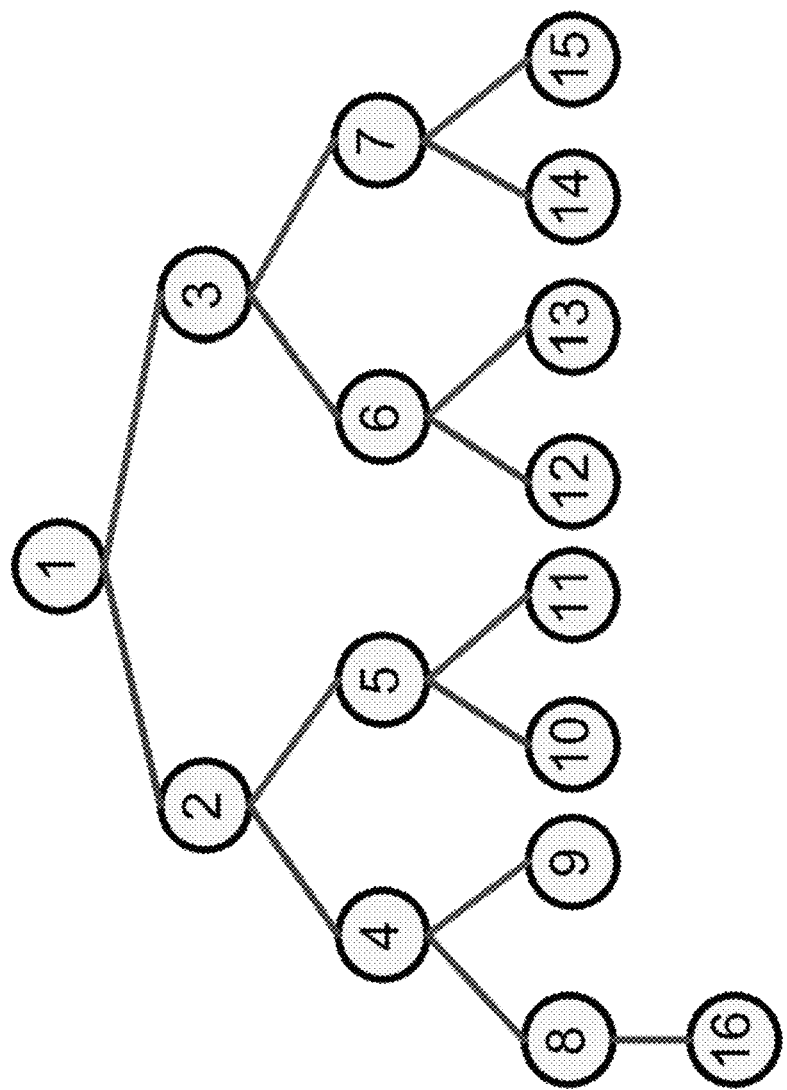
Figure 2D:
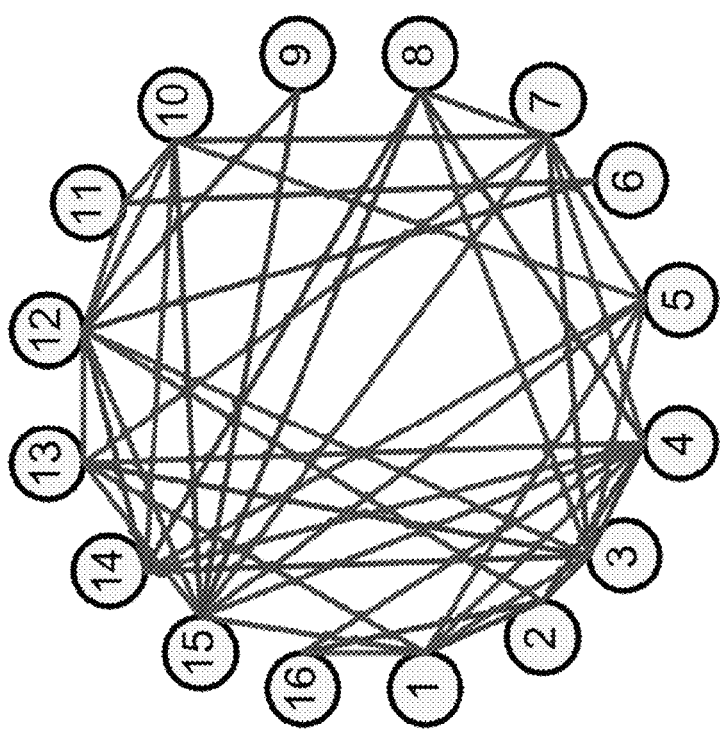
Figure 2E:
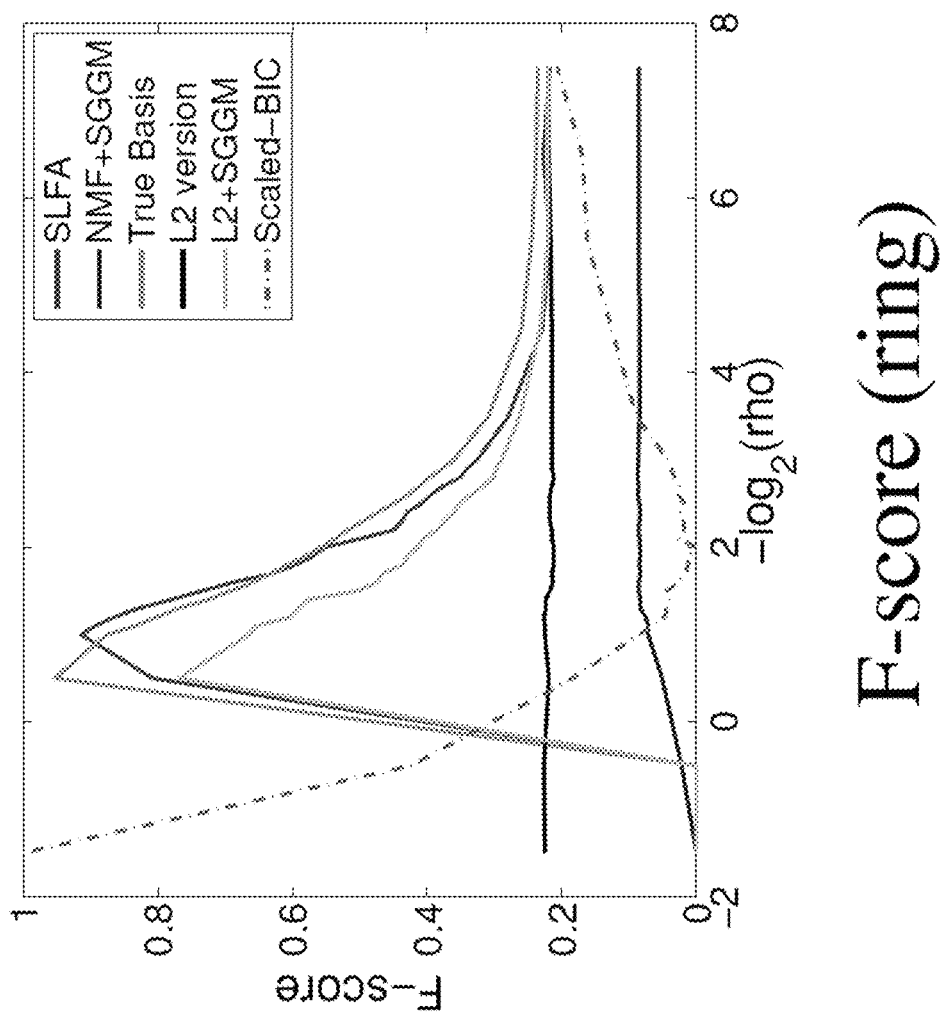
Figure 2F:
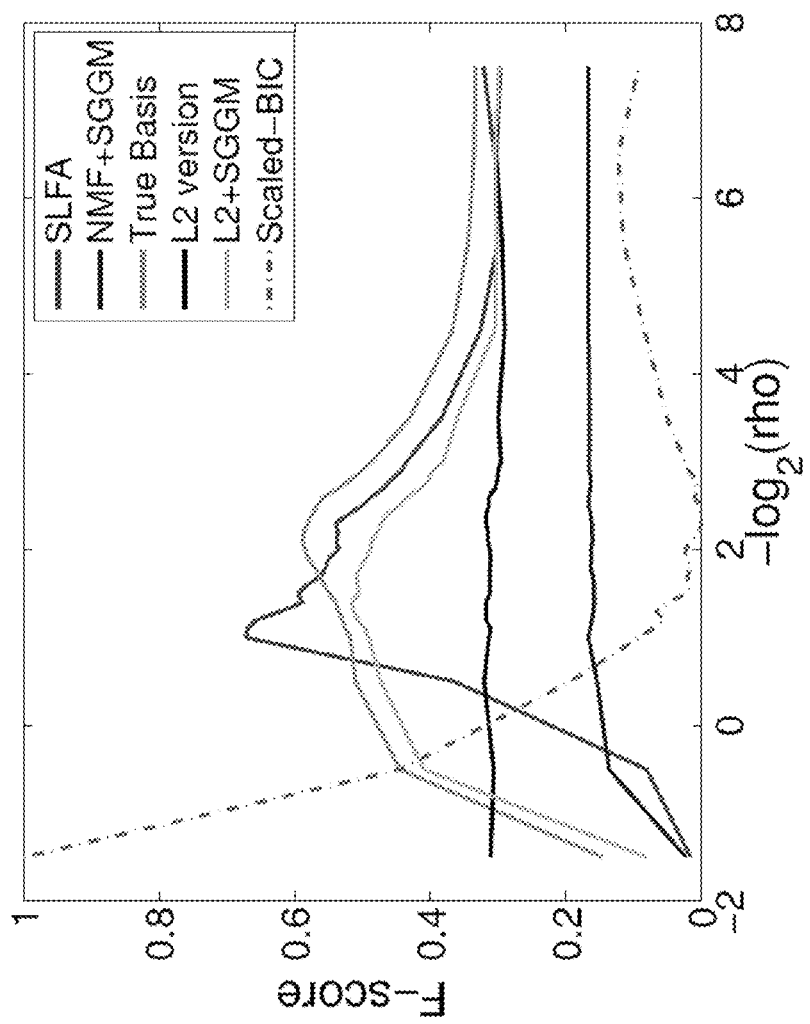
Figure 2G:
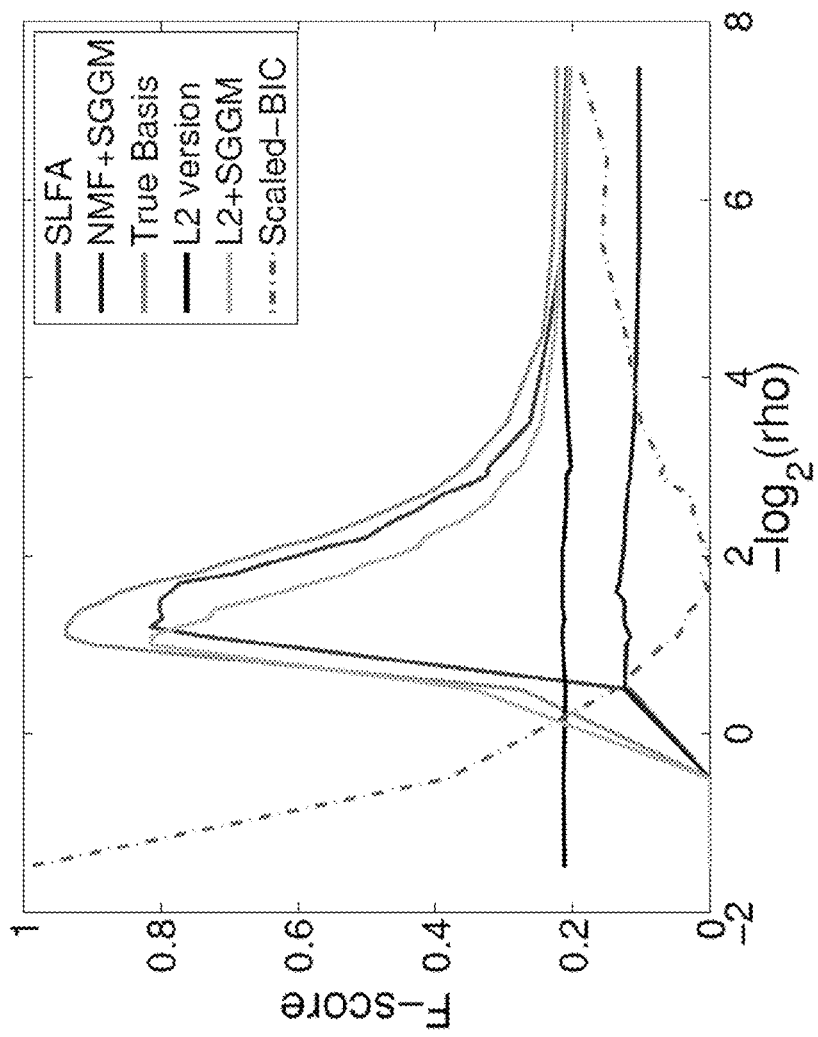
Figure 2H:
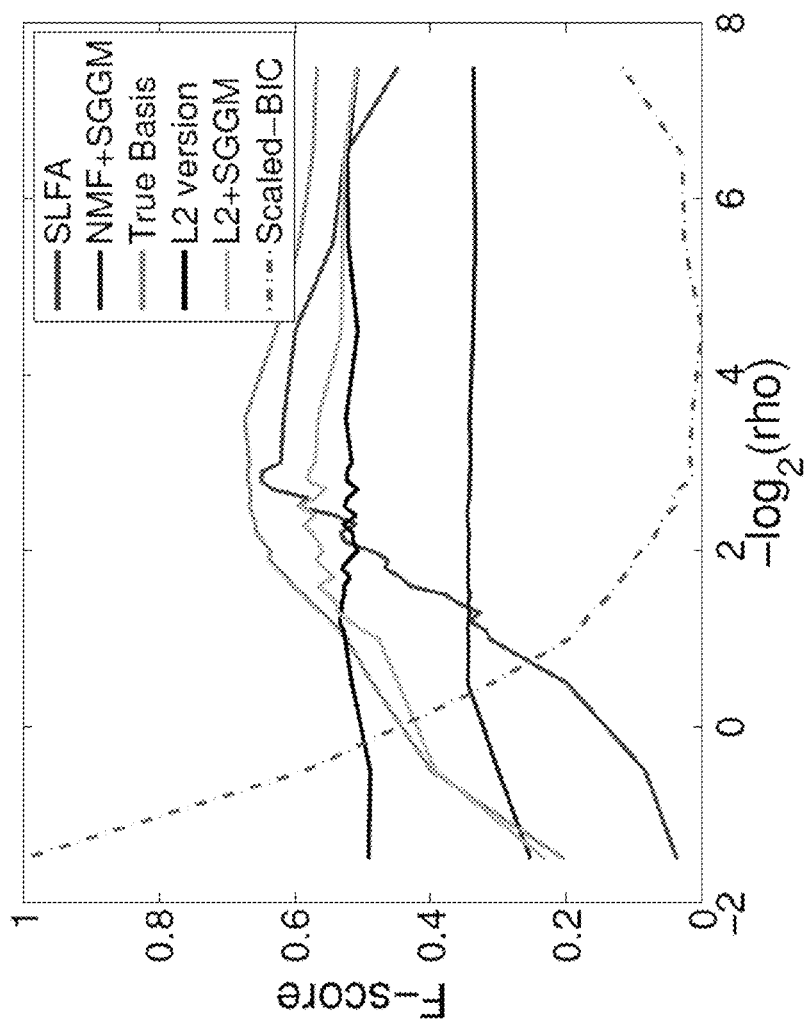

The following merely illustrates the principles of the disclosure. It will thus be appreciated that those skilled in the art will be able to devise various arrangements which, although not explicitly described or shown herein, embody the principles of the disclosure and are included within its spirit and scope.

Furthermore, all examples and conditional language recited herein are principally intended expressly to be only for pedagogical purposes to aid the reader in understanding the principles of the disclosure and the concepts contributed by the inventor(s) to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently-known equivalents as well as equivalents developed in the future, i.e., any elements developed that perform the same function, regardless of structure.

Thus, for example, it will be appreciated by those skilled in the art that the diagrams herein represent conceptual views of illustrative structures embodying the principles of the invention.

In addition, it will be appreciated by those skilled in art that any flow charts, flow diagrams, state transition diagrams, pseudocode, and the like represent various processes which may be substantially represented in computer readable medium and so executed by a computer or processor, whether or not such computer or processor is explicitly shown.

In the claims hereof any element expressed as a means for performing a specified function is intended to encompass any way of performing that function including, for example, a) a combination of circuit elements which performs that function or b) software in any form, including, therefore, firmware, microcode or the like, combined with appropriate circuitry for executing that software to perform the function. The invention as defined by such claims resides in the fact that the functionalities provided by the various recited means are combined and brought together in the manner which the claims call for. Applicant thus regards any means which can provide those functionalities as equivalent as those shown herein. Finally, and unless otherwise explicitly specified herein, the drawings are not drawn to scale.

Thus, for example, it will be appreciated by those skilled in the art that the diagrams herein represent conceptual views of illustrative structures embodying the principles of the disclosure.

Introduction

By way of some additional background, we note that data samples described in high-dimensional feature spaces are encountered in many important areas. To enable the efficient processing of large data collections, latent factor models (LFMs) have been developed to find concise descriptions of the members of a data collection. A random vector $x \in \mathbb{R}^M$ is assumed to be generated by a linear combination of a set of basis vectors, i.e.

$$x = Bs + \epsilon = B_1 s_1 + B_2 s_2 + \ldots + B_K s_K + \epsilon \qquad (1)$$

where $B = [B_1, \ldots, B_K]$ stores the set of unknown basis vectors and $\epsilon$ describes noise. The i-th "factor" ($i \in \{1, \ldots, K\}$) denotes the i-th variable in the vector s.

According to this disclosure, we consider the problem of learning hidden dependency structure of latent factors in complex data sets. Our goal includes at least two main aspects: (1) to learn the interpretable lower-dimensional representations hidden in a set of data samples, and (2) to simultaneously model the pairwise interaction of latent factors.

As those skilled in the art will readily appreciate, it is difficult to achieve both aspects at the same time using existing models. The statistical structure captured by LFM methods, such as Principal Component Analysis (PCA) are limited in interpretability, due to their anti-correlation assumption on the latent factors. For example, when a face image is represented as a linear super-position of PCA bases with uncorrelated coefficients learned by PCA, there exist complex cancellations between the basis images.

Additional methods that theoretically assume independence of components like ICA or sparse coding fail to generate independent representations in practice. Notable results in have shown that the coefficients of linear features for natural images are never independent.

Instead of imposing this unrealistic assumption, more recent works have proposed to allow correlated latent factors, which shows to be helpful in obtaining better performance on various tasks. However, the graphical structure of latent factors (i.e., conditional dependence/independence) is not considered in these works. Particularly, the sparse structure of the latent factor network is often preferred but has been never been explicitly explored in the learning process. For example, when mining the enormous number of on-line news-text documents, a method discovering semantically meaningful latent topics and a concise graph connecting the topics will greatly assist intelligent browsing, organizing and accessing of these documents.

According, one contribution of this disclosure is a general LFM method that models the pairwise relationships between latent factors by sparse graphical models. By introducing a generalized Tikhonov regularization, a method according to the present disclosure enforces the interaction of latent factors to have an influence on learning latent factors and basis vectors. As a result, a method according to the present disclosure will learn meaningful latent factors and simultaneously obtain a graph where the nodes represent hidden groups and the edges represent their pairwise relationships. This graphical representation helps one analyze collections of complex data samples in a much more structured and organized way, e.g. using the news-text as a potential application. The latent representations of data samples obtained from the model captures deeper signals hidden in the data which produces the useful features for other tasks as well as in-depth analysis, e.g. achieving a state-of-the-art performance on classifying cancer samples in our experiment.

Sparse Undirected Graphical Model of Latent Factors: A General Formulation

Our framework according to the present disclosure considers data samples drawn from the exponential family of distributions, i.e., $$p(x|\eta) = h(x) \exp(\eta^T T(x) - A(\eta)), \qquad (2)$$

where sufficient statistic $T(x) \in \mathbb{R}^M$, $\eta \in \mathbb{R}^M$ represents the natural parameter for the model, $T(x)$, $h(x)$ and $A(\eta)$ are known functions defining a particular member of the exponential family. This family includes most of the common distributions, like normal, Dirichlet, multinomial, Poisson, and many others.

To learn the hidden factors for generating x, the natural parameter $\eta$ is assumed to be represented by a linear combination of basis vectors, i.e., $$\eta = Bs, \qquad (3)$$

where $B = [B_1, \ldots, B_K]$ is the basis matrix. To model the pairwise interaction between latent factors, we introduce a pairwise Markov Random Field (MRF) prior on the vector of factors $s \in \mathbb{R}^K$:

$$p(s|\mu, \Theta) = \frac{1}{Z(\mu, \Theta)} \exp\left(-\sum_{i=1}^{K} \mu_i s_i - \frac{1}{2} \sum_{i=1}^{K} \sum_{j=1}^{K} \theta_{ij} s_i s_j\right) \qquad (4)$$

with parameter $\mu = [\mu_i]$, symmetric $\Theta = [\theta_{ij}]$, and partition function $Z(\mu, \Theta)$ which normalizes the distribution. Notably, the classic Ising model and Gaussian graphical model are two special cases of the above MRF. We let $G = (V, E)$ denote a graph with K nodes, corresponding to the K latent factors $\{s_1, \ldots, s_K\}$, and with edge set $$E = \{(i,j) \in V \times V : \theta_{ij} \neq 0\}. \qquad (5)$$

Since $\theta_{ij} = 0$ indicates that latent factor $s_i$ and latent factor $s_j$ are conditionally independent given other latent factors, the graph G presents an illustrative view of the statistical dependencies between latent factors. A schematic diagram is provided in FIG. 1 to illustrate the concept.

With such a hierarchical and flexible model as in FIG. 1, there would be significant risk of over-fitting, especially when we consider all possible interactions between K latent factors. Therefore, regularization has to be introduced for better generalization property of the model. As we will show later, regularization is also necessary from the perspective of avoiding ill-posed optimization problem. The regularization technique we use is to introduce a sparsity-inducing prior for $\Theta$:

$$p(\Theta) \propto \exp\left(-\frac{1}{2} \rho \|\Theta\|_1\right), \qquad (6)$$

where ρ is a positive hyper-parameter and $\|\Theta\|_1 := \Sigma_i \Sigma_j |\theta_{ij}|$. We aim to achieve two goals when designing such a prior distribution: (1) in practice irrelevant latent factors are not supposed to be conditionally dependent and hence a concise graphical structure between latent factors is preferred in many applications such as topic mining and image feature learning, and (2) in contrast to $L_0$ regularization which is the number of non-zero components, we obtain a convex subproblem of Θ, that can be efficiently solved by utilizing the recently developed convex optimization techniques.

Learning Algorithm

We consider the posterior distribution of parameters, which is proportional to the product of data likelihood and the prior distributions:

$$h(x)\exp\{s^\top B^\top T(x) - A(Bs)\} \times \frac{1}{Z(\mu,\Theta)} \quad (7)$$

$$\exp\left(-\mu^\top s - \frac{1}{2}s^\top \Theta s\right) \times \exp\left(-\frac{1}{2}\rho\|\Theta\|_1\right).$$

Given a set of data observations $\{x^{(1)}, \ldots, x^{(N)}\}$, the Maximum a Posteriori (MAP) estimates of the basis matrix B, the latent factors in $S=[s^{(1)}, \ldots, s^{(N)}]$ and the parameters $\{\mu, \Theta\}$ of the latent factor network are therefore the solution of the following problem $$\min_{B,S,Q} \frac{1}{N}\sum_i \{-\log h(x^{(i)}) + A(Bs^{(i)}) - s^{(i)\top}B^\top T(x^{(i)})\} + \quad (8)$$

$$\log Z(\mu,\Theta) + \frac{1}{N}\mu^\top S 1_N + \frac{1}{2N}tr(S^\top \Theta S) + \frac{1}{2}\rho\|\Theta\|_1$$

s.t. $B \geq 0$, $\|B_k\|_2 \leq 1$, $k = 1, \ldots, K$, where additional constrains $B \geq 0$ and $\|B_k\|_2 \leq 1$ are introduced for the identifiability of the model.

The objective function in the above equation (8) is not convex with respect to all three unknowns (B, S and Θ) together. Therefore, a good algorithm in general exhibits convergence behavior to a stationary point and we can use Block Coordinate Descent algorithm to iteratively update B, S and Θ as follows:

--- while not convergent do
  For i = 1, ..., N, solve $$\min_{s^{(i)}} -\log h(x^{(i)}) + A(Bs^{(i)}) - s^{(i)T}B^T T(x^{(i)}) + \mu^T s^{(i)} + \frac{1}{2}s^{(i)T}\Theta s^{(i)} \quad (9)$$

Solve $$\min_{B\geq 0, \|B_k\|_2\leq 1} \Sigma_i \{-\log h(x^{(i)}) + A(Bs^{(i)}) - s^{(i)T}B^T T(x^{(i)})\} \quad (10)$$

Solve $$\min_{\mu,Q} \log Z(\mu,\Theta) + \frac{1}{N}\mu^T S 1_N + \frac{1}{2N}tr(S^T QS) + \frac{1}{2}\rho\|\Theta\|_1 \quad (11)$$

end do

---

Since $p(x|\eta)$ is in the exponential family, the subproblem (10) with respect to B is convex and smooth with simple constraints, for which quasi-Newton methods such as projected L-BFGS are among the most efficient methods. Subproblem (9) is easy to solve for real-valued $s^{(i)}$ but generally hard when the latent factors only admit discrete values.

For example for $s \in \{0,1\}^K$ and Gaussian $p(x|\eta)$, subproblem (9) is a 0-1 quadratic programming problem and we can resort to SDP based Branch and Bound algorithms to solve it in a reasonable time. The subproblem (11) is minimizing the sum of a differentiable convex function and an $L_1$ regularization term, for which a few recently developed methods can be very efficient, such as variants of ADMM. For the cases of discrete s with large K (usually K<<M), evaluation of the partition function $Z(\mu,\Theta)$ during the iterations is #P-hard and Others [see, e.g., Schmidt] discuss methods to solve the pseudo-likelihood approximation of (11).

A Special Case: Structured Latent Factor Analysis

From this point on in this disclosure, we consider a special case of the learning problem in Eq. (8) when x follows a multivariate normal distribution and s follows a sparse Gaussian graphical model (SGGM). We name our model under this default setting as "structured latent factor analysis" (SLFA) and compare it to related works. Assume $$p(x|\eta) = (2\pi)^{-M/2}\exp\left(-\frac{1}{2\sigma^2}\|x-\eta\|^2\right)$$

and $s \sim N(\mu, F^{-1})$, with sparse precision matrix F (inverse covariance). For simplicity we assume the given data matrix $X=[x^{(1)}, \ldots, x^{(N)}]$ is centered and set $\mu=0$. Then the objective function in Eq. (8) becomes $$\min_{B,S,Q} \frac{1}{N}\|X-BS\|_\Phi^2 + \sigma^2\left(\frac{1}{N}tr(S^\top \Phi S) - \log\det(\Phi) + \rho\|\Phi\|_1\right) \quad (112)$$

s.t. $B \geq 0$, $\|B_k\|_2 \leq 1$, $k = 1, \ldots, K \Phi \succcurlyeq 0$.

If Φ is fixed, the problem in Eq. (12) is a matrix factorization method with generalized Tikhonov regularization: trace $(S^T\Phi S)$. If $\Phi_{i,j}>0$, minimizing the objective function will avoid $s_i$ and $s_j$ to be simultaneously large, and we say the i-th factor and the j-th factor are negatively related. If $\Phi_{i,j}<0$, the solution is likely to have $s_i$ and $s_j$ of the same sign, and we say the i-th factor and the j-th factor are positively related. If $\Phi_{i,j}=0$, the regularization doesn't induce interaction between $s_i$ and $s_j$ in the objective function. Therefore, this regularization term makes SLFA produce a collaborative reconstruction based on the conditional dependencies between latent factors. On one hand, the collaborative nature makes SLFA capture deeper statistical structure hidden in the data set, compared to the matrix factorization problem with the Tikhonov regularization $\|S\|_F^2$ or sparse coding with the sparsity-inducing regularization such as $\|S\|_1$. On the other hand, SLFA encourages sparse interactions which is very different from previous works such as correlated topic Model and latent Gaussian model, where the latent factors are densely related.

An On-line Algorithm For Learning SLFA:

The convex subproblem $$\min_{\Phi \succ 0} \frac{1}{N}tr(S^\top \Phi S) - \log\det(\Phi) + \rho\|\Phi\|_1 \quad (13)$$

can be efficiently solved by a recent quadratic approximation method. For subproblem of S we have closed-form solution $$S = (B^T B + \sigma^2 F)^{-1} X.$$

Moreover, considering that many modern high-dimensional data sets include a large number of data observations (e.g. text articles from web-news), we propose an online algorithm for learning SLFA on larger data sets. As summarized in Algorithm 1, below, at each iteration, we randomly fetch a mini-batch of observations simultaneously, compute their latent factor vector s. Then the latent factor vectors are used to update the basis matrix B in stochastic gradient descent fashion with projections on the constraint set. Lastly we update the precision matrix $\Phi$.

---
Algorithm 1 An on-line algorithm for learning SLFA
---

Input: X [$x^{(1)}, \ldots, x^{(N)}$], initial guess of basis matrix B, initial precision matrix $\Phi = I$, number of iterations T, parameters $\sigma^2$ and $\rho$, step-size $\gamma$, mini-batch size N'
for t = 1 to T
  Draw N' observations randomly from X = [$x^{(1)}, \ldots, x^{(N)}$] to form the matrix $X_{batch}$.
  Compute the latent factor vectors $S_{batch} = (B^T B + \sigma^2 \Phi)^{-1} X_{batch}$.
  Update the basis matrix B using a gradient descent step:

$$B \leftarrow B - \frac{\gamma}{N'}[BS_{batch} - X_{batch}]S_{batch}^T$$

Project columns of B to the first orthant and the unit ball, i.e., B ≥ 0 and $\|B_i\| \leq 1$.
  Solve the subproblem (13) to update the sparse inverse covariance matrix $\Phi$ using all available latent factor vectors in S.
end for

---

Parameter Selection:

The hyper-parameter $\rho$ controls the sparsity of $\Phi$. A large $\rho$ will result in a diagonal precision matrix $\Phi$, indicating that the latent factors are conditionally independent. As $\rho \to 0$, $\Phi$ becomes denser. However, if we set $\rho=0$, the subproblem with respect to $\Phi$ has a closed form solution $$\Phi = \left(\frac{1}{N}SS^T\right)^{-1},$$

i.e., inverse sample covariance matrix. Plugging it back to the Eq. (12), we have $$\min_{B,S} \frac{1}{N}\|X - BS\|_F^2 + \sigma^2 \text{logdet}\left(\frac{1}{N}SS^T\right),$$

which doesn't have a lower bound. Therefore the regularization is necessary and we choose positive values for $\rho$ in the experiments. For supervised tasks, we use cross-validation to choose the proper value of $\rho$ that maximizes the performance on validation set. For unsupervised applications, we combine the BIC criterion, with our model to obtain the following criterion:

$$\rho^* = \min_{\rho} \frac{1}{N}\|X - B(\rho)S(\rho)\|_F^2 + \qquad\qquad\qquad\qquad\qquad$$
$$\sigma^2\left(\frac{1}{N}tr(S(\rho)^T \Phi(\rho) S(\rho)) - \text{logdet}(\Phi(\rho)) + \frac{\log N}{N}\|\Phi(\rho)\|_0\right),$$
(14 — actually not numbered here)

where B($\rho$), S($\rho$) and F($\rho$) and learned from (12) with parameter $\rho$. Alternatively, for visual analysis of latent factors, we can select multiple values of $\rho$ to obtain $\Phi$ with desired sparsity.

Relationship to Sparse Gaussian Graphical Model:

We can also see SLFA as a generalization of sparse Gaussian graphical model. In fact, if the reduced dimension K=M, the problem (12) has trivial solution B=I and S=X, and the problem becomes the same as (13). When K<M, the subproblem with respect to s has solution $s=(B^T B+\sigma^2\Phi)^{-1}x$. Therefore, lower dimensional random vector s has less variables among which each variable is a linear combination of the original variables of x with the combination weights stored in $W=(B^T B+\sigma^2\Phi)^{-1}$. In this sense, SLFA could be seen as the sparse Gaussian graphical model of s=Wx, i.e. it generalizes the concept from the original (totally N) variables to the merged (totally K) group variables.

Several recent efforts have combined the model of SGGM and with latent factor models. For example, "Kronecker GLasso" performs a joint learning of row and column covariances for matrix-variate Gaussian models. Different from our SLFA, these methods still aim at modeling the interaction between the original features and doesn't consider interaction in the latent factor space. Instead, SLFA is a hierarchical model and the learned pairwise relationships are on the latent factor level. If we apply both SLFA and Kronecker GLasso on a text corpus where each document is represented by a 50,000 sparse vector and number of latent factors (topics) are fixed as 50, then Kronecker GLasso will produce a precision matrix of dimension 50,000×50,000 and a corresponding sparse graph of 50,000 nodes. SLFA, however, can dramatically reduce the problem to learning a 50×50 sparse precision matrix and the corresponding graph of 50 nodes.

Relationship to Other Works:

Sparse coding can be modeled as:

$$\min_{B,S} \frac{1}{2}\|X - BS\|_F^2 + \lambda\|S\|_1. \qquad (14)$$

For many high-dimensional data sets such as text in natural languages and genes in biological data sets, the input data is already very sparse or high dimensional. Thus, sparse coding is not easily applicable. Intuitively, sparse coding tries to remove the redundancy in the representation of data while SLFA encourages a (sparse) collaborative reconstruction of the data from the latent bases.

Recently, Jenatton et al. proposed a method that can learn latent factors with given tree structure. The optimization problem in Jenatton et al., is a penalized matrix factorization problem similar to our Eq. (12) and Eq. (14), but uses a different regularization term which imposes the overlapped group sparsity of factors. Differently, SLFA can learn a more general graphical structure among latent factors and doesn't assume that data sample maps to a sparse combination of basis vectors.

The model of SLFA has similar hierarchy with correlated topic model and latent Gaussian model. Besides the key difference of sparsity, SLFA directly use precision matrix to learn latent factor networks while the other two works learn the covariance matrix by Bayesian methods.

Experiments

We now conduct experiments on both synthetic and real world data sets to show that: (1) SLFA recovers latent basis vectors and finds the pairwise relationships of latent factors, (2) SLFA generates useful features for various tasks such as images analysis, topic visualization and microarray analysis.

Synthetic Data I: Four Different Graphical Relationships

The first experiment uses randomly generated synthetic data with different graphical structures of latent factors. It aims to test if SLFA can find true latent factors and the true relationships among latent factors and to study the effect of the parameter $\rho$ on the results. We use four special cases of Sparse Gaussian Graphical Model to generate the latent factors. The underlying graph is either a ring, a grid, a tree or a random sparse graph, which are shown in FIGS. 2(a)-(h). A sparse positive definite matrix $\Phi^* \in \mathbb{R}^{10 \times 10}$ is constructed based on the graph of SGGM. Then we sample 200 Gaussian random vectors, $s^{(1)}, \ldots, s^{(200)} \in \mathbb{R}^{10}$ with precision matrix $\Phi^*$. A set of vectors $B^* \in \mathbb{R}^{500 \times 10}$ randomly generated with normal distribution and then filtered by a sigmoid function $$f(b) = \frac{1}{1 + e^{-100b}}$$

such that most components of $B^*$ are close to either 0 or 1. $B_1$, $B_2, \ldots, B_{10}$ are then normalized as basis vectors. Finally, the synthetic data points are generated by $x^{(i)} = Bs^{(i)} + 0.1\epsilon_i$, $i = 1, \ldots, 200$, where $\epsilon_i \sim N(0, I)$.

We compare SLFA to other four methods for learning the basis matrix B and the precision matrix $\Phi$ from the data. The first one is NMF, where we learn nonnegative basis B from the data and then learn the sparse precision matrix $\Phi$ for the corresponding factor vectors (non nonnegative constraint on factors) by SGGM. The second one is an ideal case where we have the "oracle" of the true basis $B^*$, then after fit the data to be true basis we learn the sparse precision matrix $\Phi$ by SGGM. The third one is named $L_2$ version of SLFA as we replace the $L_1$ regularization of $\Phi$ by a Frobenius norm regularization. The fourth method first applies L2 version of SLFA and then learns $\Phi$ by SGGM. In all cases except the oracle method, we have a non-convex problem so that after we obtain the learned basis vectors we use Hungarian algorithm to align them to with the true basis vectors based on the cosine similarity. We compute the precision and recall rates for recovering the relationship between latent factors by comparing the learned $\Phi$ with the true precision matrix $\Phi^*$.

We plot F-score based on the precision and recall rates averaged over 10 experiments. As may be observed from FIG. 2, when $\rho$ is large, the estimated $\Phi$ is diagonal so that recall rate is 0. As $\rho$ becomes smaller, more nonzero elements appear in the estimated $\Phi$ and both the recall and precision rate of "positive/negative relationship" get increased. When $\rho$ is small enough, the recovered $\Phi$ becomes denser and may not even recover the "positive/negative relationship" correctly. We can see that for all four cases, our proposed method SLFA is as good as the "oracle" method at recovering the pairwise relationship between latent factors. NMF most probably fails to find the right basis since it does consider any higher level information about the interactions between basis elements, hence SGGM can't find meaningful relationship between the factors obtained from NMF. $L_2$ version of SLFA also has poor F-score since it can't recover the sparse structure. Since latent factors have dense interactions in $L_2$ version of SLFA, combining it with a postprocessing by SGGM improves the performance significantly, however it still performs worse compared to SLFA. This experiment also confirms that the idea of performing an integrated learning of the bases together with a regularized precision matrix is essential for recovering the true structure in the data.

Synthetic Data II: Parts-Based Images

Figure 3A:
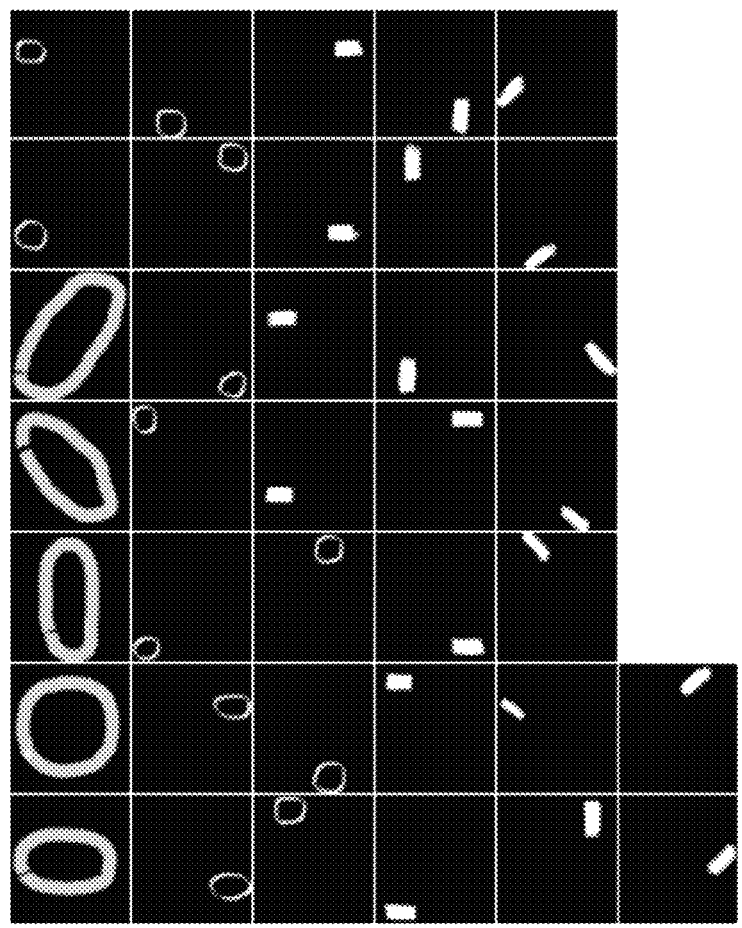
FIG. 3($a$)-3($e$) is a series of graphs showing F(I,j) values and corresponding Bi and Bj elements learned by SLFA for the six highest and six lowest entries in F according to an aspect of the present disclosure.
Figure 3B:
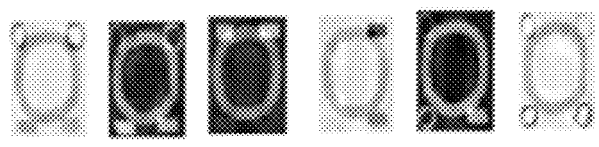
Figure 3B:
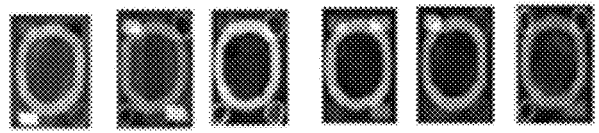
Figure 3B:
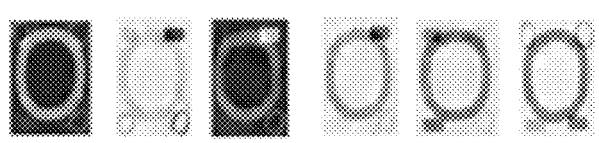
Figure 3B:
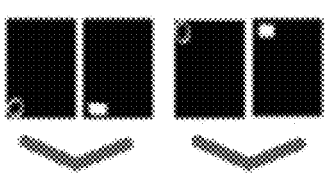
Figure 3B:
Figure 3B:
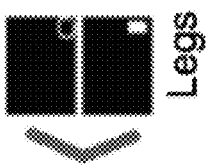
Figure 3C:
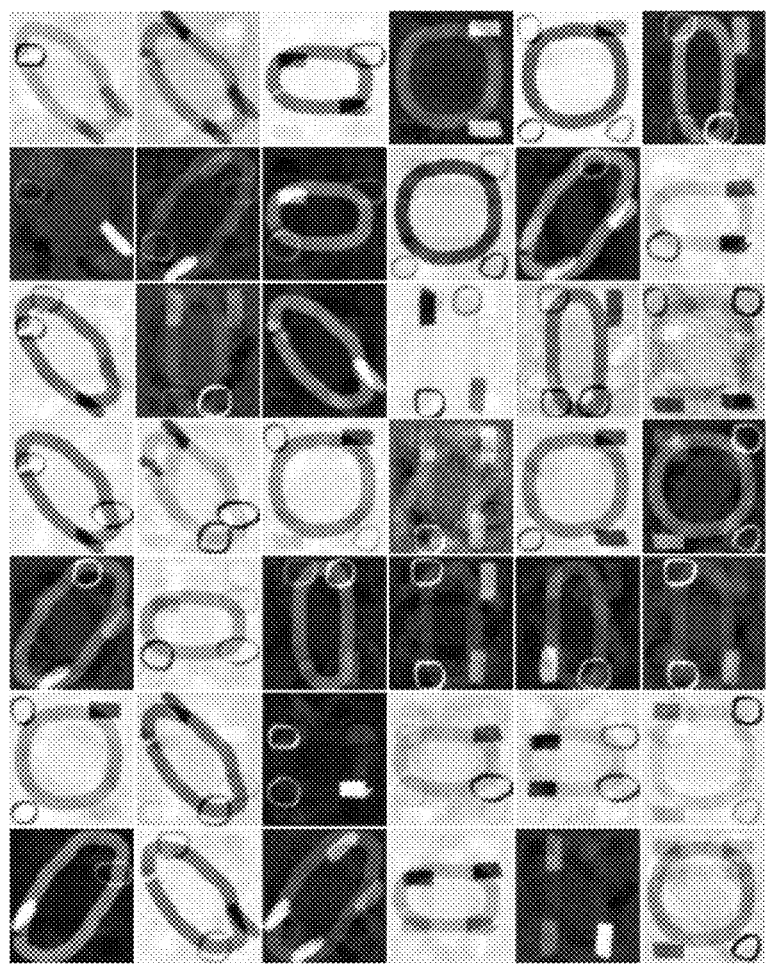

The second experiment also utilizes a simulated data set based on images to compare SLFA with popular latent factor models. We set up an experiment by generating 15000 images of "bugs", each of which is essentially a linear combination of five latent parts shown in FIG. 3(a). Given 37 basis images, we first randomly select one of the five big circles as the body of the "bugs". Each shape of body is associated with four positions where the legs of the bug is located. We then randomly pick 4 legs from its associated set of 4 small circles and 4 small squares. However, for each leg, circle and square are exclusive of each other. We combine the selected five latent parts with random coefficients that are sampled from the uniform distribution and multiplied by −1 with probability 0.5. Finally, we add a randomly selected basis with small random coefficients plus Gaussian random noise to the image to introduce the noise and confusion in the data set. A few examples of the bug image samples created by the above strategy are shown in FIG. 3(c). The generating process (FIG. 3(b) indicates positive relationship between one type of body and its associates legs, as well as negative relationship between the pair of circle and square that is located at the same position.

Figure 3E:
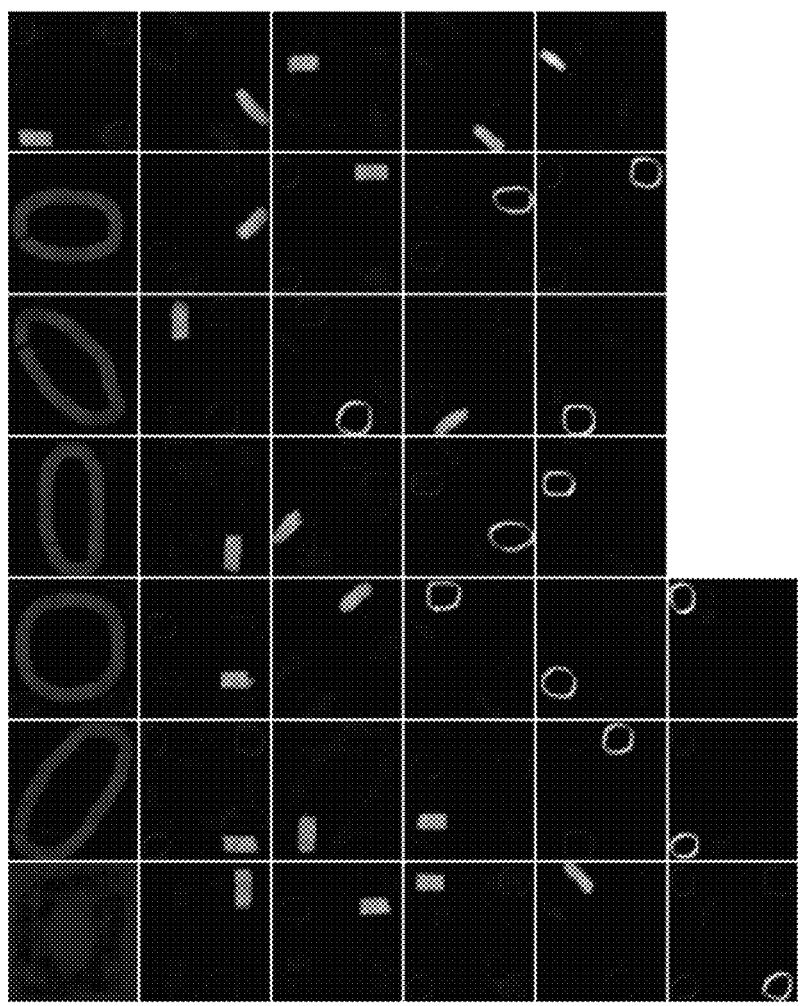

Using SLFA and other two baseline algorithms, PCA and NMF, we learn a set of latent bases and compare the result of three methods in FIG. 3(e). We can see that the basis images generated by SLFA is almost exactly same as the true latent bases. This is due to the fact that SLFA accounts for the sparse interaction between factors in the joint optimization problem and encourages collaborative reconstruction. NMF basis (shown in supplementary material due to space considerations) in this case also turns out to be similar to true basis, however, one can still observe that many components contain mixed structures since it can not capture the true data generation process. The bases learned by PCA (also shown in supp. material) is not interpretable as expected.

More importantly, SLFA provides the convenience of analyzing the relationship between the bases using the precision matrix $\Phi$. In FIG. 3(d), we analyze the relational structure learned in the precision matrix $\Phi$. The most negatively related (exclusive) pairs (the i and j entries with highest positive entries in $\Phi$) are circular and square legs which conforms fully to the generation process, since only one of them is chosen for any given location. Accordingly, the most positively related pairs are a body shape and one of its associated legs since every bug has a body and four legs with fixed positions.

Real Data I: NIPS Documents

We now apply SLFA to the NIPS corpus which contains 1740 abstracts from the NIPS Conferences 1-12 for the purpose of topic/content modeling. SLFA is used to organize and visualize the relationship between the structured topics. SLFA is applied on the 13649 dimensional tf-idf feature vector which is normalized to have the unit norm. We fix the number of topics to be 40 and tune the parameters σ and ρ to obtain Φ with a proper sparsity for the visualization task.

Figure 4:
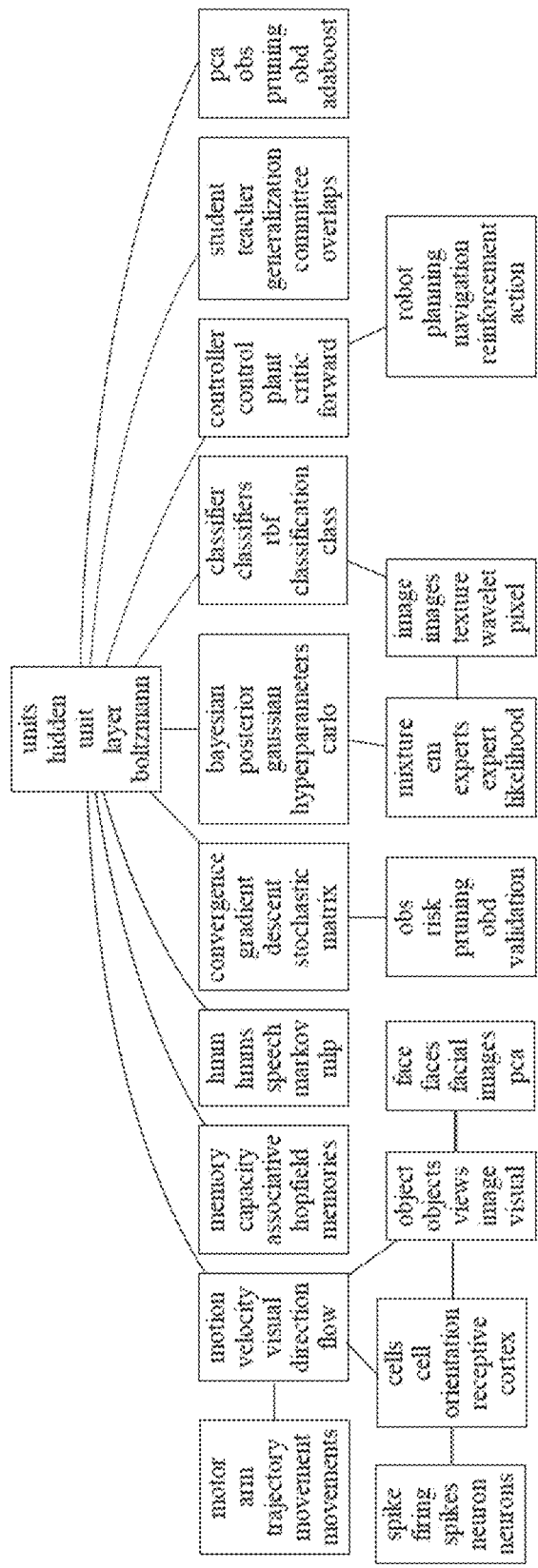
FIG. 4 is a chart showing positively related topics learned by SLFA discovered from NIPS text corpus wherein each edge corresponds to a negative element in the sparse precision matrix F according to an aspect of the present disclosure.
Figure 5:
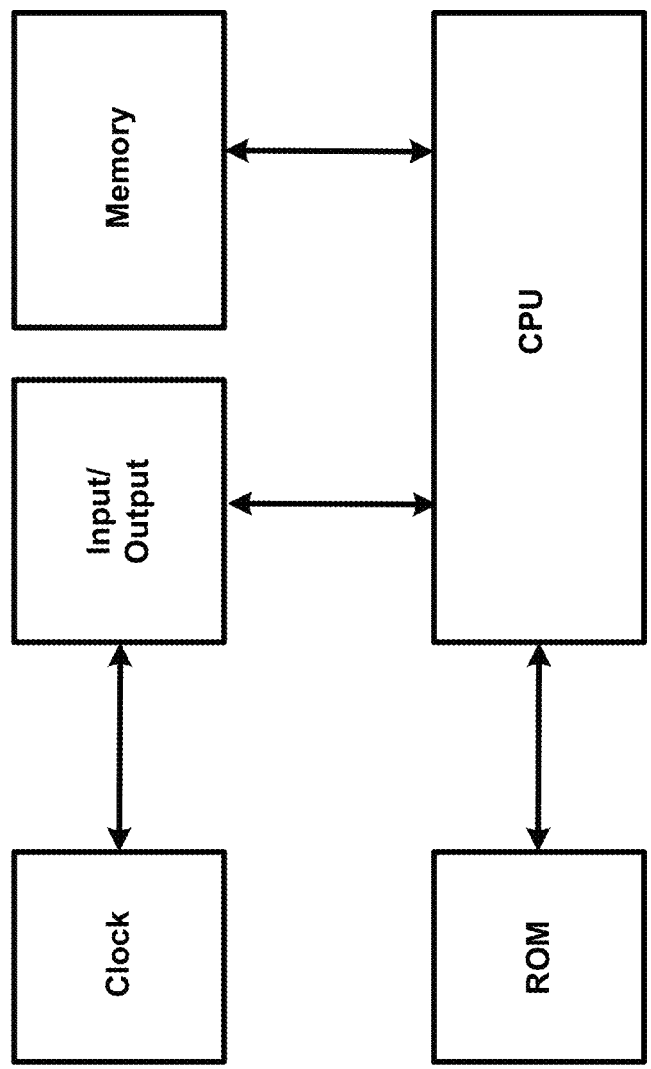
FIG. 5 is a schematic block diagram depicting a contemporary computer system that may advantageously execute methods according to the present disclosure.

In FIG. 4, we plot a graph of topics (standing-alone topics removed) with positive interaction between each other and present the top 5 keywords for each topic. For example, the topic at the top is about general notions in many learning algorithms and acts as the hub point of the graph. more specific words that are relevant to a particular learning algorithm or a more specialized topic of interest. It is obvious that SLFA not only extracts the underlying topics, but is also able to capture the (de)correlations between topics. For example, on the far left, the topic related to cells is connected to "motion, velocity, . . . ", "objects, image, . . . " and "spike, neurons, . . . " nodes. This subgraph clearly represents a few topics in computer vision and neuroscience. The node on the far right containing "robot, planning, . . . " is connected to the node with "controller, control, . . . " which represents a robotics related topic-cluster. It is also interesting to note that SLFA can obtain a graph of negatively related topics (shown in supplementary material). One can see that closely related topics tend to exclude each other.

Real Data II: Gene Microarray Data for Cancer Classification

Next, we test our model on a classification task which uses breast cancer microarray data set. This data set contains the gene expression values of 8,141 genes for 295 breast cancer tumor samples. The task is to classify the tumor samples into two classes (with 78 metastatic and 217 non-metastatic).

Using the classification error rates as the metric, we compare totally five methods, including Lasso, Lasso-overlapped-group, linear SVM classifier, PCA with linear SVM classifier and SLFA with linear SVM classifier. Lasso-overlapped-group, which is a logistic regression approach with the graph-guided sparsity enforced, uses a known biological network as the graphical (overlapped group) regularization on the lasso regression. The other methods, including SLFA, do not use this extra supervised information. We run 10-fold cross validation and use the averaged error rate to indicate the predictive performance of different methods. The test is repeated 50 times and each time all methods use the same split of training and validation sets.

TABLE 1

| SLFA | Lasso Overlapped Group | Lasso | SVM | PCA |
|---|---|---|---|---|
| 34.22 ± 2.58 | 35.31 ± 2.05 | 36.42 ± 2.50 | 36.93 ± 2.54 | 36.85 ± 3.02 |

The averaged cross-validation error rate is shown in Table 1. Shown in Table 1 are cross-validation error rate(s) (average and standard deviation) by different methods on Gene Microarray data. We can observe that SLFA (K=100) has lower error rates than other methods, including Lasso, SVM and PCA. Compared to the method of Lasso-overlapped-group which constructs the regularization from external information (42,594 known edges as prior knowledge), our method based on SLFA performs better, even though it does not utilize any extra evidence. This is a strong evidence which indicates that SLFA can extract deeper structural information hidden in the data. Indeed, genes naturally act in the form of functional modules (gene groups) to carry out specific functions. Gene groups that usually correspond to biological processes or pathways, exhibit diverse pairwise dependency relationships among each other. SLFA discovers these relationships while learning the latent representation of each data sample at the same time. That is why its learned lower-dimensional representation captures more fundamental and strong signals, and achieves the state-of-art classification performance. The learned structural information and latent gene groups also get confirmed by the biological function analysis in supplementary document.

Conclusion

As may now be readily appreciated, we have presented a structured latent factor model that simultaneously learns latent factors and their pairwise relationships. The model is formulated to represent data drawn from the general exponential family of distributions. The learned sparse interaction between latent factors is crucial for understanding complex data sets and to visually analyze them. SLFA model is also a hierarchical extension of Sparse Gaussian Graphical Model by generalizing the application of precision matrix from the original variable space to the latent factor space and optimizing the bases together with the precision matrix simultaneously. We have also provided an efficient online learning algorithm that can scale SLFA training to large-scale datasets and showed that SLFA not only can predict the true basis and structured relationship between bases, but also it can achieve state-of-the-art results in challenging biological classification task.

The foregoing is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that those skilled in the art may implement various modifications without departing from the scope and spirit of the invention. Those skilled in the art could implement various other feature combinations without departing from the scope and spirit of the invention. paper we have introduced a novel structured latent factor model that simultaneously learns latent factors and their pairwise relationships. The model is formulated to represent data drawn from the general exponential family of distributions. The learned sparse interaction between latent factors is crucial for understanding complex data sets and to visually analyze them. SLFA model is also a hierarchical extension of Sparse Gaussian Graphical Model by generalizing the application of precision matrix from the original variable space to the latent factor space and optimizing the bases together with the precision matrix simultaneously. We have also provided an efficient online learning algorithm that can scale SLFA training to large-scale datasets and showed that SLFA not only can predict the true basis and structured relationship between bases, but also it can achieve state-of-the-art results in challenging biological classification task.

The invention claimed is:

1. A computer implemented method of structured latent factor analysis comprising:
    by a computer:
    learning one or more hidden dependency structures of latent factors of a set of data;
    modeling pairwise relationships among them and determining structural relationships through the use of a sparse Gaussian graphical model;
    outputting an indication of the latent factor relationships;
    wherein said pairwise relationship modeling is performed according to the following pairwise Markov Random Field (MRF) prior on a vector of factors $s \in \mathbb{R}^K$:

$$p(s|\mu, \Theta) = \frac{1}{Z(\mu, \Theta)} \exp\left(-\sum_{i=1}^{K} \mu_i s_i - \frac{1}{2} \sum_{i=1}^{K} \sum_{j=1}^{K} \theta_{ij} s_i s_j\right) \quad (4)$$

with parameter $\mu=[\mu i]$, symmetric $\Theta=[\theta_{ij}]$, and partition function $Z(\mu,\Theta)$ which normalizes the distribution, wherein p is a probability of a field configuration of $(s|\mu, \Theta)$, K is a number of latent factors, s is an element of natural parameter $\mathbb{R}^K$, and i and j are non-zero variables; and modeling the pairwise interaction simultaneously with the learning one or more hidden dependency structures of latent factors of a set of data.

2. The computer implemented method of claim 1 wherein said model identifies a dependency structure in the latent space.

3. The computer implemented method of claim 1 wherein said model is determined by a unidirected graphical model.

\* \* \* \* \*